US00PP08491P

United States Patent [19]

Laver

[11] Patent Number: Plant 8,491

[45] Date of Patent: Dec. 14, 1993

[54] MINIATURE ROSE PLANT NAMED 'LAVDOL'

[75] Inventor: Keith Laver, Ontario, Canada

[73] Assignee: The Conard-Pyle Company, West Grove, Pa.

[21] Appl. No.: 963,384

[22] Filed: Oct. 19, 1992

[51] Int. Cl.[5] ..... A01H 5/00

[52] U.S. Cl. ..... Plt./7.1

[58] Field of Search ..... Plt. 7.1

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which abundantly forms on a uniform basis attractive long-lasting double blossoms which are of a very stable Peach/Apricot coloration. The plant is well adapted to forcing while grown in small containers, and is particularly well suited for use as a flowering pot plant when grown indoors or outdoors. Additionally, the plant is not particularly affected by cryptogamic diseases.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) was the Painted Doll variety (nonpatented in the United States). The male parent (i.e., the pollen parent) of the new variety also was the Painted Doll variety. The parentage of the new variety can be summarized as follows:

Painted Doll × Painted Doll.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms in abundance on a uniform basis attractive double long-lasting blossoms which are of a very stable Peach/Apricot coloration,
(b) forms fairly vigorous vegetation,
(c) exhibits a bushy and compact growth habit,
(d) is well adapted to forcing while growing in small containers, and
(e) is not particularly affected by cryptogamic diseases.

The new variety well meets the needs of the horticultural industry. It is particularly well-suited for use as attractive ornamentation as a flowering pot plant when grown indoors or outdoors. The blossom coloration is very stable and the flowering is very uniform.

The new variety has been found to undergo asexual propagation at West Grove, Pa., U.S.A., by a number of routes, including budding, grafting, cuttage, etc. The characteristics of the new variety have been found to be strictly transmissible by such asexual propagation from one generation to another.

The new variety has been named the Lavdol variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during September while growing in containers on their own roots in the greenhouse at West Grove, Pa., U.S.A.

At the top (far left) is shown a specimen of a young flowering shoot. At middle (far left) is shown a specimen of a flowering branch with four buds. At the bottom (far left) are shown specimens of two main branches. At the top (middle) are shown specimens of four buds which illustrate the opening progression from left to right. Below the four buds is illustrated a specimen of a young shoot. At the middle also are illustrated specimens of blooms in progressive stages of opening with the newly opened blooms being shown at the top and the fully open blooms being shown at the bottom wherein the obverse generally is shown at the left and the reverse at the right. At the right are illustrated specimens of leaves with three, five, and seven leaflets with the upper surfaces being shown on the left and the under surfaces being shown on the right.

DETAILED DESCRIPTION

The chart used in the identification of the colors is that of The Royal Horticultural Society (R.H.S. Colour Chart). The terminology in common terms sometimes also is employed. The description is based on one year old specimens of the new variety which were observed during September while growing in containers on their own roots in the greenhouse at West Grove, Pa., U.S.A.

Class: Miniature.

Plant:

*Height.*—Approximately 12 to 15 inches when grown in one-gallon containers.

*Habit.*—Bushy.

Branches:

*Color.*—Young stems: reddish green. Adult wood: Yellow-Green Group 146A, and strongly tinted with reddish coloration.

*Thorns.*—Size: average. Quantity: low. Color: pinkish with a yellowish tip.

Leaves:

*Petioles.*—Upper surface: striped, reddish brown on young foliage and medium green on mature foliage with glandular edges. Under surface: smooth, and light green.

*Stipules.*—Adnate, pectinate, wide and linear.

*Leaflets.*—Number: 3, 5 (most often), and 7. Shape: elliptic. Serration: single and regular. Texture: consistent. General appearance: dense and bright foliage. Color (young foliage): Upper surface: Green Group 143B with reddish edges. Under surface: Green Group 138B. Color (adult foliage): Upper surface: dark green, Green Group 137A. Under surface: greyish green, Greyed-Green Group 191A.

Inflorescence:

*Number of flowers.*—Approximately 1 to 4 blooms per stem, and usually 1 or 2 per stem.

*Peduncle.*—Light green, straight, rigid, smooth, bears a few prickles, and its length is approximately 1 inch on average.

*Sepals.*—Upper surface: tomentose and greenish in coloration. Under surface: light to medium green, and the outer sepals have glandular edges, and sometimes end with a leaf-like appendix.

*Buds.*—Shape: oval. Length: approximately ½ in. on average. Size: large. Color upon opening: Upper surface: Peach, Orange Group 29C, and edged with Orange Group 29A. Under surface: Shrimp Red, Orange-Red Group 33C, and widely suffused with Yellow Group 2B near the attachment of the petal.

*Flower.*—Form: as a flat cup at opening, and double. Diameter: approximately 1½ in. on average. Color (when opening begins): Upper surface: Shrimp Red, Orange-Red Group 33D. Under surface: Apricot, Orange-Red Group 24D, and edged with Peach, Orange Group 29C. Color (when blooming): Upper surface: Shrimp Red, Orange Group 33D. Under surface: light Peach, Orange Group 29D, turning toward the center of the petals to Apricot, Orange-Red Group 24D. Color (at end of blooming): Upper surface: light Shrimp Red, Orange-Red Group 33D. Under surface: light Peach, Orange Group 29D, turning toward the center of the petals to light Apricot, Orange-Red Group 24D. Fragrance: very slight. Lasting quality: long. Petal number: approximately 38 to 40 on average. Petal shape: round, and curling outward when fully open. Petal texture: consistent. Petal drop: good. Anthers: yellowish/straw in coloration, of irregular heights, and in the form of a circle at the edge of the receptacle. Stamen number: approximately 155 to 170 on average. Filaments: normal and straw colored. Pistil number: approximately 25 on average. Stigmas: normal and tan colored. Styles: greenish in coloration with light fuchsia tips, very short, twisted, tomentose, and of irregular heights. Receptacle: light green, smooth, and in longitudinal section it is in the shape of a funnel at the dehiscence of the anthers.

Development:

*Vegetation.*—Fairly vigorous.

*Blooming.*—Abundant and very uniform.

*Resistance to diseases.*—Good.

I claim:

1. A new and distinct variety of miniature rose plant characterized by the following combination of characteristics:

(a) forms in abundance on a uniform basis attractive double long-lasting blossoms which are of a very stable Peach/Apricot coloration,
(b) forms fairly vigorous vegetation,
(c) exhibits a bushy and compact growth habit,
(d) is well adapted to forcing while growing in small containers, and
(e) is not particularly affected by cryptogamic diseases;

substantially as herein shown and described.

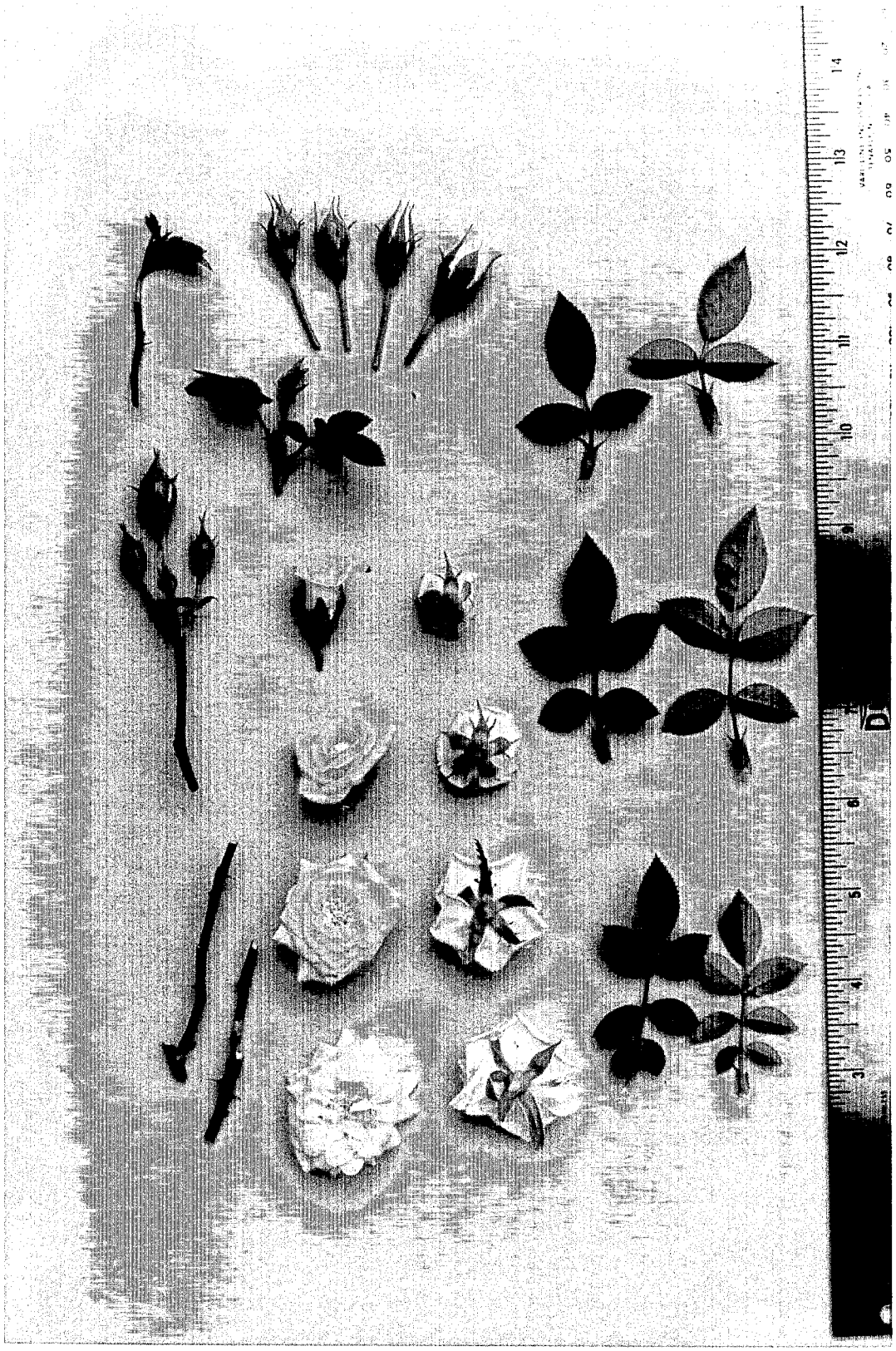

* * * * *